United States Patent [19]

Yoshikawa et al.

[11] Patent Number: 5,369,015
[45] Date of Patent: Nov. 29, 1994

[54] METHOD FOR PRODUCING AN ANGIOTENSIN CONVERTING ENZYME INHIBITOR-CONTAINING COMPOSITION

[75] Inventors: Masaaki Yoshikawa, Joyo; Keiichi Yokoyama; Masayasu Hasegawa, both of Kyoto; Ryouichi Yasumoto, Kawachinagano; Hiroyuki Fujita, Suita, all of Japan

[73] Assignee: Nippon Gohsei Kagaku Kogyo Kabushiki Kaisha, Osaka, Japan

[21] Appl. No.: 960,636

[22] Filed: Oct. 14, 1992

[30] Foreign Application Priority Data

Oct. 17, 1991 [JP] Japan .................. 3-298061

[51] Int. Cl.$^5$ ............ A61K 37/02; C07K 5/06; C12P 21/00
[52] U.S. Cl. ............................. 435/68.1; 426/7; 514/2; 514/15; 514/17; 530/314; 530/316; 530/328; 530/330; 435/212
[58] Field of Search .............. 435/68.1, 212; 530/314, 530/316, 328, 330; 514/2, 15, 17; 426/7

[56] References Cited

U.S. PATENT DOCUMENTS

| | | | |
|---|---|---|---|
| 3,857,966 | 12/1974 | Feldman et al. | 426/7 |
| 3,932,672 | 1/1976 | Pour-El et al. | 435/68.1 |
| 4,107,334 | 8/1978 | Jolly | 426/7 |
| 4,212,889 | 7/1980 | Fuentevilla | 426/7 |
| 4,584,197 | 4/1986 | Takasaki | 435/68.1 |
| 5,238,921 | 8/1993 | Maruyama et al. | 530/330 |

FOREIGN PATENT DOCUMENTS

| | | | |
|---|---|---|---|
| 1189810 | 7/1985 | Canada | 435/68.1 |
| 2817144 | 10/1978 | Germany | 435/68.1 |
| 58-109425 | 6/1983 | Japan . | |
| 58-177920 | 10/1983 | Japan . | |
| 59-44323 | 3/1984 | Japan . | |
| 59-44324 | 3/1984 | Japan . | |
| 61-36226 | 2/1986 | Japan . | |
| 61-36227 | 2/1986 | Japan . | |
| 0742463 | 6/1980 | U.S.S.R. | 435/68.1 |

*Primary Examiner*—Herbert J. Lilling
*Attorney, Agent, or Firm*—Armstrong, Westerman, Hattori, McLeland & Naughton

[57] ABSTRACT

Disclosed is a method for producing an angiotensin converting enzyme inhibitor composition from natural materials, which composition is of use as an antihypertensive drug or diet. The method comprises heating a meat in water at a temperature not lower than 50° C. to extract water-soluble protein and hydrolyzing the residue predominantly composed of water-insoluble protein with a protease.

1 Claim, No Drawings

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( D ) TOPOLOGY: linear (i i) MOLECULE TYPE: peptide (v i) ORIGINAL SOURCE:
    (A) ORGANISM: Mammalian Tissue (x i) SEQUENCE DESCRIPTION: SEQ ID NO:1:

```
Asp Arg Val Tyr Ile His Pro Phe His Leu
1               5                   10
```

(2) INFORMATION FOR SEQ ID NO:2:

(i) SEQUENCE CHARACTERISTICS:
        (A) LENGTH: 5 amino acids
        (B) TYPE: amino acid
        (D) TOPOLOGY: linear (i i) MOLECULE TYPE: peptide (v i) ORIGINAL SOURCE:
        (A) ORGANISM: Mammalian meat, fish, crustaceans (x i) SEQUENCE DESCRIPTION: SEQ ID NO:2:

```
Ile Trp His His Thr
1               5
```

(2) INFORMATION FOR SEQ ID NO:3:

(i) SEQUENCE CHARACTERISTICS:
        (A) LENGTH: 5 amino acids
        (B) TYPE: amino acid
        (D) TOPOLOGY: linear (i i) MOLECULE TYPE: peptide (v i) ORIGINAL SOURCE:
        (A) ORGANISM: Mammalian meat, fish, crustaceans (x i) SEQUENCE DESCRIPTION: SEQ ID NO:3:

```
Ala Leu Pro His Ala
1               5
```

(2) INFORMATION FOR SEQ ID NO:4:

(i) SEQUENCE CHARACTERISTICS:
        (A) LENGTH: 3 amino acids
        (B) TYPE: amino acid
        (D) TOPOLOGY: linear (i i) MOLECULE TYPE: peptide (v i) ORIGINAL SOURCE:
        (A) ORGANISM: Mammalian meat, fish, crustaceans (x i) SEQUENCE DESCRIPTION: SEQ ID NO:4:

```
Ile Lys Trp
1
```

METHOD FOR PRODUCING AN ANGIOTENSIN CONVERTING ENZYME INHIBITOR-CONTAINING COMPOSITION

FIELD OF THE INVENTION

The present invention relates to a method of producing an angiotensin converting enzyme (hereinafter referred to briefly as ACE) inhibitor-containing composition from naturally occurring materials, which composition is of use as, inter alia, an antihypertensive agent or antihypertensive diet.

BACKGROUND OF THE INVENTION

Angiotensin converting enzyme (ACE) is an enzyme which is chiefly present in the lung, vascular endothelial cells and renal proximal tubules and acts on angiotensin I (Asp-Arg-Val-Tyr-Ile-His-Pro-Phe-His-Leu) (Sequence I) SEQ I to cleave a dipeptide ($His^9$-$Leu^{10}$) off its C-terminus to give rise to angiotensin II which has potent pressor activity.

Furthermore, this enzyme decomposes bradykinin, a physiological hypotensive substance, to inactivate it and, as such, is intimately involved in the pressor system. It has been considered that inhibition of ACE would lower the blood pressure and is, therefore, clinically useful for the prevention and treatment of hypertension.

Recently, since captopril, a proline derivative, was synthesized and found to have hypotensive activity, much research has been undertaken for synthesizing a variety of ACE inhibitors and it has also been attempted to isolate such substances from natural resources.

This is because natural type ACE inhibitors available from foods or food materials may be expected to be of value as antihypertensive agents of low toxicity and high safety.

However, it is rare that a potent ACE inhibitor is found in natural resources and all that are known at present are teprotide (a nonapeptide, SQ 20881) which was isolated from Brazilian and Japanese snake venoms and Metabolite IS83 of a Streptomyces organism. (Japanese Patent Laid-open No. 58-177920). As ACE inhibitors obtainable by enzymatic treatment of a natural material, the peptides obtainable by hydrolysis of milk casein with trypsin (Japanese Patent Laid-open No. 58-109425, No. 59-44323, No. 59-44324, No. 61-36226 and No. 61-36227) are known. Under the circumstances, development of new, more potent ACE inhibitors has been earnestly awaited.

SUMMARY OF THE INVENTION

In their search for an ACE inhibitor of natural origin with a low risk of adverse effects, the inventors of the present invention found that peptides having exceptionally high ACE inhibitory activity are present in the composition which is obtainable by heat-treating a meat material, particularly fish meat, pork, beef or poultry meat, in water at a temperature not lower than 50° C. to extract water-soluble protein and hydrolyzing the residue-predominantly composed of water-insoluble protein with a protease, particularly thermolysin or pepsin.

DETAILED DESCRIPTION OF THE INVENTION

The production method according to the invention is characterized in that a material meat is heat-treated in water at a temperature not lower than 50° C. and the residue after extraction of water-soluble protein, which is hence predominantly composed of water-insoluble protein, is utilized. This method provides a composition having very potent ACE inhibitory activity.

In accordance with the invention, residues of protein extraction which have heretofore claimed little commercial values and been either discarded or used only as organic fertilizers, viz. large quantities of extraction residues available in the production of natural condiments from fish meat, secondary products of fish meat, crustacean meat, pork, poultry meat, beef, etc., can be effectively reclaimed and utilized and, therefore, the invention is of significant industrial value.

This invention can be carried into practice by using any of known proteases, such as thermolysin, pepsin, trypsin, chymotrypsin, etc. as well as other proteases of microbial origin, although the use of thermolysin or pepsin is conducive to particularly beneficial results.

Thermolysin is a protease produced by *Bacillus thermoproteolyticus*, and pepsin is one of acid proteases secreted in the stomach.

The material meat may be any animal meat, such as fish meat, shellfish meat, pork, beef, poultry meat and so on. Particularly useful are bonito and materials derived from bonito.

In accordance with the method of the invention, a material meat is heat-treated in water at a temperature not lower than 50° C. with stirring for about 1 minute to 3 hours to extract out water-soluble protein and provide a residue predominantly composed of water-insoluble protein.

The above residue is mixed with hot water and, where necessary, homogenized with vigorous agitation. Then, based on the substrate protein, 0.0005 to 10 weight % of the enzyme preparation is added. The pH of the system is adjusted to pH 2-6 in the case of an acid protease, pH 5-9 in the case of a neutral protease, or pH 7-12 in the case of an alkaline protease, and the reaction is carried out at 5° to 90° C., either under stationary conditions or with stirring, for 1 minute to 48 hours, preferably 30 minutes to 10 hours, until a peptide decomposition rate of at least 5% is attained. The peptide decomposition rate (rate of cleavage of peptide bonds) is expressed in the percentage of amino nitrogen relative to total nitrogen. The method for determination is described in Journal of Agricultural and Food Chemistry 24 No. 6 1090–1093 (1976).

The resulting ACE inhibitor composition is a mixture of various peptides, chiefly of the amino acid sequence of Ile-Trp-His-His-Thr SEQII (Sequence II), Ala-Leu-Pro-His-Ala SEQ II (Sequence II) or Ile-Lys-Trp SEQ IV (Sequence IV). This mixture may be used as it is or further purified for use.

The route of administration of the peptide composition of the invention may be oral, parenteral or rectal, although the oral route is preferred.

The dosage of the peptide(s) according to the invention is dependent on the species of compounds involved, the method of administration, the patient's age and condition, etc. but is generally 0.001 to 1000 mg and preferably 0.01 to 100 mg. This dose can be administered once to 3 times a day. The peptides according to the invention are generally administered as formulated with pharmaceutical carriers and excipients which are commonly used in the pharmaceutical industry and inert to the peptides of the invention. Among such carriers and excipients are lactose, glucose, mannitol, dextrin, cyclodextrin, starch, sucrose, magnesium metasilicate aluminate, synthetic aluminum silicate, carboxymethylcellulose sodium, hydroxypropyistarch, carboxymethylcellulose calcium, ion exchange resins, methylcellulose, gelatin, gum arabic, hydroxypropylcellulose, hydroxypropylmethylcellulose, polyvinylpyrrolidone, polyvinyl alcohol, soft silicic anhydride, magnesium stearate, talc, gum tragacanth, bentonite, B gum, titanium dioxide, sorbitan fatty acid esters, sodium lauryl sulfate, glycerol, glycerol fatty acid esters, purified lanolin, glycerogelatin, polysorbate, macrogols, vegetable oils, waxes, liquid paraffin, white petrotatum, fluorocarbons, nonionic surfactants, propylene glycol, water and so on.

The dosage form may be a tablet, capsule, granule, powder, syrup, suspension, suppository, ointment, cream, gel, cataplasma, inhalant, or injectable solution. These preparations can be manufactured by the established pharmaceutical procedures. In the case of a liquid preparation, it may be a lyophilizate or the like which is extemporaneously reconstituted with a suitable vehicle such as water. The tablet and granule may be coated in the conventional manner. In the case of an injection, it can be prepared by dissolving the peptides of the invention in water. Where necessary, the peptides may be dissolved in physiological saline or a glucose solution. Such solutions may contain a buffer, a preservative and/or other additives.

These preparations may contain the peptides of the invention in a proportion of not less than 0.01% by weight and preferably 0.5 to 70% by weight. These preparations may further contain other therapeutically useful ingredients.

In accordance with the present invention, an ACE inhibitor composition of value as an antihypertensive agent or diet can be produced from naturally occurring materials.

EXAMPLES

The following examples are further illustrative of the invention.

Example 1

Five grams of dried bonito flakes were heat-treated in how water at 90° C. for 15 minutes to extract water-soluble protein and filtered through a 200-mesh screen to give a residue predominantly composed of water-insoluble protein. This residue was thoroughly homogenized with 40 ml of water and thermolysin or pepsin was allowed to act on the homogenate. The reaction mixture was then boiled at 100° C. for 10 minutes and then allowed to stand. The ACE inhibitor activity in the supernatant was then assayed.

Conditions of Enzymatic Reaction

The reaction mixture was previously adjusted to pH 7.0 with sodium hydroxide when thermolysin was used or to pH 1.6 with hydrochloric acid when pepsin was used. The temperature of the enzymatic reaction was 60° C. for thermolysin and 37° C. for pepsin. In both cases, the reaction was conducted under stationary conditions for 5 hours.

Each protease was added at the level of 1 weight % relative to the substrate protein.

Assay of ACE Inhibitor Activity

The assay of ACE inhibitor activity was carried out in accordance with the method of Cheung and Cushman [Biochemical Pharmacology 20, 1637 (1971)] under the following conditions.

Substrate: Bz(benzyl)-Gly-His-Leu
(86 mg dissolved in 8 ml water - 8 ml phospahte buffer (500 mM, pH 8.3) containing 1.5 mM NaCl)

Enzyme: Rabbit lung acetone powder (Sigma)
(1 g milled in 10 ml of 50 mM phosphate buffer (pH 8.3) and centrifuged; the supernatant was used)

Thus, 100 μl of the above substrate and 12 μl of the enzyme solution were mixed with a predetermined amount of the peptide mixture of the invention followed by addition with sufficient water to make 250 μl. The enzymatic reaction was conducted at 37° C. for 30 minutes and, then, quenched with 250 μl of 1N-HCl. After addition of 1.5 ml of ethyl acetate, the reaction mixture was stirred in a vortex mixer for 15 seconds and, then, centrifuged. A 1.0 ml portion of the ethyl acetate layer was taken and the ethyl acetate was distilled off. The residue was dissolved in 1 mt of distilled water and the absorbance ($OD_{228}$) of extracted hippuric acid at 228 nm was measured.

The inhibitory activity was expressed as the 50% inhibitory concentration [$IC_{50}$(μg/ml)] of the inhibitor (the peptide of the invention) with the $OD_{228}$ value in the absence of the inhibitor being taken as 100% ACE activity and the $OD_{228}$ value of the reaction system at reaction time 0 as 0%.

The results are shown in Table 1.

Comparative Example 1

The procedure of Example 1 was repeated except that solid-liquid separation after extraction of water-soluble protein was not performed. Thus, thermolysin or pepsin was allowed to act on the mixture of the extract and residue and the ACE inhibitor activity was assayed as in Example 1. The results are shown in Table 1.

Comparative Example 2

The procedure of Example 1 was repeated except that thermolysin or pepsin was permitted to act on the extract obtained after solid-liquid separation and the ACE inhibitor activity was determined as in Example 1. The results are shown in Table 1.

TABLE 1

| | $IC_{50}$ (μg/ml) | |
|---|---|---|
| | Thermolysin | Pepsin |
| Example 1 | 55 | 270 |
| Comparative Example 1 | 110 | 700 |
| Comparative Example 2 | ≧2000 | ≧2000 |

Example 2

The procedure of Example 1 was repeated except that 6.0 g of chicken was used in lieu of dried bonito flakes and the amount of protease based on substrate protein was 0.8 weight % for thermolysin or 1.5 weight for pepsin. The results are shown in Table 2.

Comparative Example 3

The procedure of Example 2 was repeated except that solid-liquid separation was not performed after extraction of water-soluble protein and thermolysin or pepsin was permitted to act on the mixture of extract and residue. The ACE inhibitor activity was assayed as in Example 2. The results are also shown in Table 2.

Comparative Example 4

The procedure of Example 2 was repeated except that thermolysin or pepsin was permitted to act on the extract obtained by solid-liquid separation following extraction of water-soluble protein and the ACE inhibitor activity was assayed as in Example 2. The results are shown in Table 2.

TABLE 2

|  | $IC_{50}$ (μg/ml) | |
| --- | --- | --- |
|  | Thermolysin | Pepsin |
| Example 2 | 71 | 205 |
| Comparative Example 3 | 125 | 850 |
| Comparative Example 4 | $\geq 2000$ | $\geq 2000$ |

Example 3

The procedure of Example 1 was repeated except that 6.5 g of pork was used in lieu of dried bonito flakes and the proportion of protease to substrate protein was 1.0 weight % for both thermolysin and pepsin. The results are shown in Table 3.

Comparative Example 5

The procedure of Example 3 was repeated except that thermolysin or pepsin was permitted to act on the mixture of extract and residue after extraction of water-soluble protein and the ACE inhibitor activity was assayed in the same manner. The results are shown in Table 3.

Comparative Example 6

The procedure of Example 3 was repeated except that thermolysin or pepsin was permitted to act on the extract obtained by solid-liquid separation after extraction of water-soluble protein and the ACE inhibitor activity of the reaction mixture was assayed in the same manner. The results are shown in Table 3.

TABLE 3

|  | $IC_{50}$ (μg/ml) | |
| --- | --- | --- |
|  | Thermolysin | Pepsin |
| Example 3 | 100 | 253 |
| Comparative Example 5 | 159 | 930 |
| Comparative Example 6 | $\geq 2000$ | $\geq 2000$ |

Example 4

The procedure of example 1 was repeated except that 7.0 g of shrimp was used in lieu of dried bonito flakes and the proportion of protease to substrate protein was 0.5 weight % for both thermolysin and pepsin. The results are shown in Table 4.

Comparative Example 7

The procedure of Example 4 was repeated except that thermolysin or pepsin was permitted to act on the mixture of extract and residue after extraction of water-soluble protein and the ACE inhibitor activity was assayed in the same manner. The results are shown in Table 4.

Comparative Example 8

The procedure of Example 4 was repeated except that thermolysin or pepsin was permitted to act on the extract obtained by solid-phase separation after extraction of water-soluble protein and the ACE inhibitor activity was assayed in the same manner. The results are shown in Table 4.

TABLE 4

|  | $IC_{50}$ (μg/ml) | |
| --- | --- | --- |
|  | Thermolysin | Pepsin |
| Example 4 | 105 | 250 |
| Comparative Example 7 | 210 | 370 |
| Comparative Example 8 | $\geq 2000$ | $\geq 2000$ |

Example 5

The procedure of Example 1 was repeated except that 8.0 g of shortnecked clam meat was used in lieu of dried bonito flakes and the proportion of protease to substrate protein was set at 0.5 weight % for both thermolysin and pepsin. The results are shown in Table 5.

Comparative Example 9

The procedure of Example 5 was repeated except that thermolysin or pepsin was permitted to act on the mixture of extract and residue after extraction of water-soluble protein and the ACE inhibitor activity was assayed in the same manner. The results are shown in Table 5.

Comparative Example 10

The procedure of Example 5 was repeated except that thermolysin or pepsin was permitted to act on the extract obtained by solid-phase separation after extraction of water-soluble protein and the ACE inhibitor activity was assayed in the same manner. The results are shown in Table 5.

TABLE 5

|  | $IC_{50}$ (μg/ml) | |
| --- | --- | --- |
|  | Thermolysin | Pepsin |
| Example 5 | 120 | 255 |
| Comparative Example 9 | 190 | 680 |
| Comparative Example 10 | $\geq 2000$ | $\geq 2000$ |

What is claimed is:

1. A method of producing an angiotensin converting enzyme inhibitor-containing composition which comprises heat-treating a dried bonito meat in water at a temperature not lower than 50° C. to extract water-soluble protein and hydrolyzing the residue predominantly composed of water-insoluble protein with a thermolysin.

* * * * *